United States Patent [19]
Craig et al.

[11] Patent Number: 5,951,837
[45] Date of Patent: Sep. 14, 1999

[54] COMPOSITION AND METHOD FOR MANUFACTURING ION SELECTIVE ELECTRODE SENSORS

[75] Inventors: Alan Robert Craig, Wilmington, Del.; James David Hamerslag, West Chester, Pa.

[73] Assignee: Dade Behring Inc., Deerfield, Ill.

[21] Appl. No.: 08/891,417

[22] Filed: Jul. 9, 1997

Related U.S. Application Data

[62] Division of application No. 08/668,223, Jun. 21, 1996, abandoned.

[51] Int. Cl.$^6$ .................................................. G01N 27/333
[52] U.S. Cl. .................. 204/416; 204/418; 204/419; 250/458.1; 356/237; 356/256; 356/317; 356/388; 427/10; 427/58
[58] Field of Search .................... 204/403, 416, 204/418, 419; 427/10, 58; 250/458.1; 356/237, 256, 317, 388

[56] References Cited

U.S. PATENT DOCUMENTS

| | | | |
|---|---|---|---|
| 4,186,020 | 1/1980 | Wachtel | 106/22 |
| 4,454,007 | 6/1984 | Pace | 204/1 T |
| 4,892,640 | 1/1990 | Wolfbeis et al. | 204/416 |
| 4,983,817 | 1/1991 | Dolash et al. | 235/462 |
| 5,095,204 | 3/1992 | Novini | 250/233 B |
| 5,284,568 | 2/1994 | Pace et al. | 204/403 |
| 5,401,377 | 3/1995 | Shieh et al. | 204/418 |
| 5,459,325 | 10/1995 | Heuton et al. | 250/458.1 |
| 5,461,136 | 10/1995 | Krutak et al. | 528/289 |
| 5,522,978 | 6/1996 | Pace et al. | 204/418 |

FOREIGN PATENT DOCUMENTS

| | | | |
|---|---|---|---|
| 0 319 873 A2 | 6/1989 | European Pat. Off. . | |
| 0 319 873A2 | 6/1989 | European Pat. Off. | G01N 33/49 |
| 0 654 664 | 5/1995 | European Pat. Off. | G01N 27/333 |
| 0 654 664 A2 | 5/1995 | European Pat. Off. . | |
| WO 87 00286 | 1/1987 | WIPO | G01N 27/28 |
| WO 87/00286 | 1/1987 | WIPO . | |
| WO 95 30148 | 11/1995 | WIPO | G01N 31/22 |
| WO 95/30148 | 11/1995 | WIPO . | |

OTHER PUBLICATIONS

Responses of Site–Controlled, Plasticized Membrane Electrodes, Linder et al., Analytical Chemistry, vol. 60, No. 4, pp. 295–301, Feb. 15, 1988.

Ion–Selective Electrodes, Foreman et al., Automatic Chemical Analysis, Ellis Horwood Ltd., Chichester, England, 1975, pp. 74–81.

Lindner, et al.; *Analytical Chemistry;* Responses of Site–Controlled, Plasticized Membrane Electrodes; 60:295–301; Feb. 15, 1988.

Foreman, et al.; *Automatic Chemical Analysis;* 2.5—Ion selective Electrodes; Pub: Ellis Horwood Limited, Chichester, England, ©1975; pp. 74–81.

*Primary Examiner*—T. Tung
*Attorney, Agent, or Firm*—Leland K. Jordan; Lois K. Ruszala

[57] ABSTRACT

This invention pertains to fluorophoric compositions of a 7-amino-coumarin derivative and methods of their use for enhancing visualization of various constituents of ion selective electrodes.

1 Claim, 10 Drawing Sheets

COMPOSITION AND METHOD FOR MANUFACTURING ION SELECTIVE ELECTRODE SENSORS

This is a division of application Ser. No. 08/668,223, filed on Jun. 21, 1996, now abandoned.

BACKGROUND OF THE INVENTION

1. Field of the Invention

The present invention pertains to optical inspection of products produced during automated manufacturing. More particularly, this invention relates to a method for tagging semi-transparent polymeric layers contained in a multilayer sensor structure in order to facilitate optical inspection and alignment of the layers.

2. Description of the Related Art

In the health care field, particularly in the area of clinical diagnostics, ion-selective-electrode (ISE) sensors are commonly used to measure the activity or concentration of various ions and metabolites present in biological fluids. ISE sensors employ potentiometric or amperiometric electrochemical processes which generate potential or current signals that are related to the activity of an ion of interest in a sample. For example, ISE sensors are typically used to determine chloride, potassium, lithium, calcium, magnesium, carbonate, hydrogen, and sodium ion content in such fluids. Generally, the signal generated within the sensor is linearly dependent on the logarithm of the activity of the ion of interest for potentiometric analyses. The activity of an ion of interest is defined as its concentration multiplied by an activity coefficient, where the activity coefficient is generally known or is available in the art.

Typically, solid state ISE sensors use a solid membrane as a sensing element or electrode, the membrane being highly selective to the ionic species being sought and reacting to the ionic species with changes in ionic conductivity. In addition, conventional ISE sensors may contain an internal reference electrode. In operation, one surface of the sensing membrane is immersed in a biological sample solution of ions for which it is selective whereby a potential develops across the membrane surface at the interface of the solution and the membrane. In a potentiometric sensor, this potential varies with the concentration of ions in solution and its magnitude is measured as a voltage. By comparing the voltage generated at the sensing membrane surface with that generated by a reference electrode using a reference ionic solution, it is possible to calculate the concentration of the ionic species being sought. The desired selectivity is often achieved by incorporating into the membrane of an ion-selective electrode an ion selective agent such as an ionophore to increase the permeability of cell membranes to a specific ion. Generally, ion-selective membranes are formed from a heavily plasticized polymer matrix, such as polyvinyl chloride, which contains the ionophore selective for the ion of interest. For example, the ionophore valinomycin has been incorporated into a layer of membrane selective for potassium ions; trifluoroacetyl-p-butylbenzene or other trifluoroacetophenone derivatives have been used as ionophores selective for carbonate ions.

By "biological sample" is meant any fluid of biological origin including fluids of biological origin which have been chemically and/or physically treated, diluted, or concentrated prior to analysis. Examples of biological samples include serum, urine, plasma, whole blood, cerebrospinal fluid, amniotic fluid, saliva and tears.

A general discussion of the principles of ISE sensors is provided by Foreman et al., "Ion Selective Electrodes", Automatic Chemical Analysis, Ellis Horwell Ltd., Chichester, England (1975). ISE sensors can be classified according to the nature of the membrane material, and include solid state membrane electrodes, glass membrane electrodes, liquid membrane electrodes having charged ion-selective agents, and neutral liquid membrane electrodes having membranes formed from an organic solution containing an electrically neutral, ion-selective agent such as an ionophore held in an inert polymer matrix.

Conventional ISE sensors are typically bulky and tend to require an undesirable large volume of biological fluid. For these reasons, much attention has been directed towards developing ISE sensors of smaller size. These relatively smaller ISE sensors can be inexpensively mass produced using techniques similar to those employed in the manufacture of multilayer electronic components, which techniques include for example, photolithography and screen printing as described in U.S. Pat. No. 4,454,007. Such ISE sensors may be in the form of a disposable cartridge or sensor assembly for use in an chemical analyzer and are generally produced on a planar substrate with plural reference elements and plural sensor elements formed thereon. Electrical contacts are positioned on the substrate face for each element, and a flow channel is typically positioned over the substrate reference and sensor elements to direct the sample being analyzed over the sensor elements. Liquid conduits are adapted to supply biological samples to the flow channel and to remove them from the ISE sensor device. The ISE sensor substrate is advantageously chosen to be of a structurally rigid material that exhibits negligible distortion when pressure is applied from the flow channel member, and is an electrical insulator to provide support for the layers of a multilayer ion sensor. A preferred material for the substrate is alumina.

The manufacture of a complete ISE sensor includes numerous sequential manufacturing steps in which the patterns within adjacent layers produced during successive manufacturing process must be aligned properly with patterns produced by preceding processes. These successive manufacturing steps are fairly complex in nature and may include conventional screen printing using a screening or photographic mask, and firing processes of paste-like compositions to produce the desired performance. The pattern and structure of the sensor resulting from each step of these many sequential operations must be accurately aligned with patterns and structures generated in preceding process steps. A misregistration of a single operation may result in an electrical open or short circuit in the finished sensor.

The use of finer and finer grids and closely spaced features as found in modern ISE sensors requires a very high degree of positional accuracy of imprinted features. Consequently, misregistration of pattern features on the panels that may occur from misalignment of the panel and screening mask or machine tool in any singular step of the multi-step manufacturing process is a particularly critical problem in contributing to manufacturing yields. Due to the importance of maintaining correct registration of all the features generated by the sequence of manufacturing steps throughout the manufacturing process, modern ISE sensors must be inspected frequently at various stages of their manufacturing.

In order to improve the accuracy of inspection during sequential manufacturing of multilayer devices in mass produced quantities, machine vision systems are frequently employed. Machine vision systems acquire an image of a selected portion of the device through an electronic sensor and determine the existence of any extraneous features or marks in the image and the acceptability of any such marks by use of a computer. The technology commonly employs a solid state CCD (charge coupled device) or MOS (metal oxide semiconductor) type black and white or color television camera. Other components of a machine vision system normally include a lens that is attached to the television camera, as well as mirrors, beam splitters (partially silvered mirrors that can reflect and transmit light at the same time), color filters, polarizers, etc. These additional components can be used to enhance contrast and/or to reduce the effect of unwanted information, to obtain the needed optical geometric arrangement in a limited space, to acquire the image, to acquire and store a two-dimensional image, and to process and analyze the image by some form of computer. Machine vision systems can also provide important and accurate process control information to help identify "problem area (s)" of the sequential manufacturing process so they may be corrected to improve quality and yield.

In the design of ISE sensors, many of the solid membranes that are selective to the ionic species being sought comprise a polymeric membrane composition that is essentially optically undistinguished from a surrounding or underlying material, i. e., is translucent, is semi-transparent, or has an optical reflectivity essentially similar to that of the surrounding material. Consequently, the integrity, pattern and outline of the imprinted membrane layer pattern may not be readily differentiated by machine vision systems. In such instances, it is known to tag the material to be identified using fluorescent compounds that are more readily capable of detection. The use of fluorescent techniques to detect the presence of compounds is known in the art. With fluorescent scanning, tagged samples are stimulated by a light beam at an excitation wavelength and the resulting stimulated fluorescent emission is examined. The stimulated fluorescent typically occurs at a different wavelength or wavelength band than the excitation wavelength. See, for example, U.S. Pat. No. 5,459,325, "High Speed Fluorescent Scanner", Hueton et als. A light source which is capable of emitting light in the near-infrared illuminates the material to be inspected and an optical filter is used to select only the wavelengths emitted by the tagging fluorescing compound.

U.S. Pat. No. 4,983,817 relates to reading a luminescent and substantially transparent bar code on a background whose reflectance may vary. Electrical signals corresponding to light reflections from both luminescent and nonluminescent portions of the bar code are processed to provide a final signal that is decoded to provide the desired reading.

U.S. Pat. No. 4,186,020 describes development of fluorescent inks that can be activated by ultraviolet light to fluoresce at longer wavelengths in instances when the background fluorescence is less.

U.S. Pat. No. 5,095,204 presents a system and method for treating or modifying bulk materials or formed articles such that they can be seen and identified under ultraviolet radiation without a permanent alteration of their appearance or properties.

U.S. Pat. No. 5,461,136 relates to a method for "marking" or "tagging" a thermoplastic polymeric material by incorporating one or more near infrared fluorescing compounds therein and a method for separating or sorting a mixture of thermoplastic containers such as bottles. Also provided are thermoplastic polymer compositions tagged with such compounds or residues as well as certain new compounds useful as near infrared fluorophoric markers.

However, a shortcoming in the application of conventional machine vision systems to the inspection of sensor membranes is the degradation in performance of the sensor membranes due to the inclusion of fluorescing compounds to make them optically discernible. The selectivity and sensitivity of an ISE sensor membrane are critically dependent upon its chemical constituents and their relative balances. Consequently, there has developed a need for a chemically inert ingredient such as a fluorophore which may be added to the sensor membrane in a quantity that does not interfere with the analytical performance of the sensor but which provides the needed fluorescence to distinguish properly aligned layers as well as identify membrane defects resulting from the manufacturing process.

SUMMARY OF THE INVENTION

The present invention addresses the problems of the prior art machine vision analysis techniques by providing a polymer composition comprised of fluorescing compounds or residues and articles comprising such compositions useful for making a layer of material readily capable of detection by using such compositions. Also provided are coumarin compounds useful as fluorophoric markers in the practice of this invention. The compositions of the present invention thus provide an improved mechanism for visualizing various constituents of sensors so that they can be examined and evaluated, and so that the process for their manufacture may be optimized, without detracting from the performance of the sensor.

BRIEF DESCRIPTION OF THE DRAWINGS

The invention will be better understood with reference to the several drawings, in which like reference numerals are used to indicate like components, in which.

DETAILED DESCRIPTION OF THE INVENTION

Figure 1:
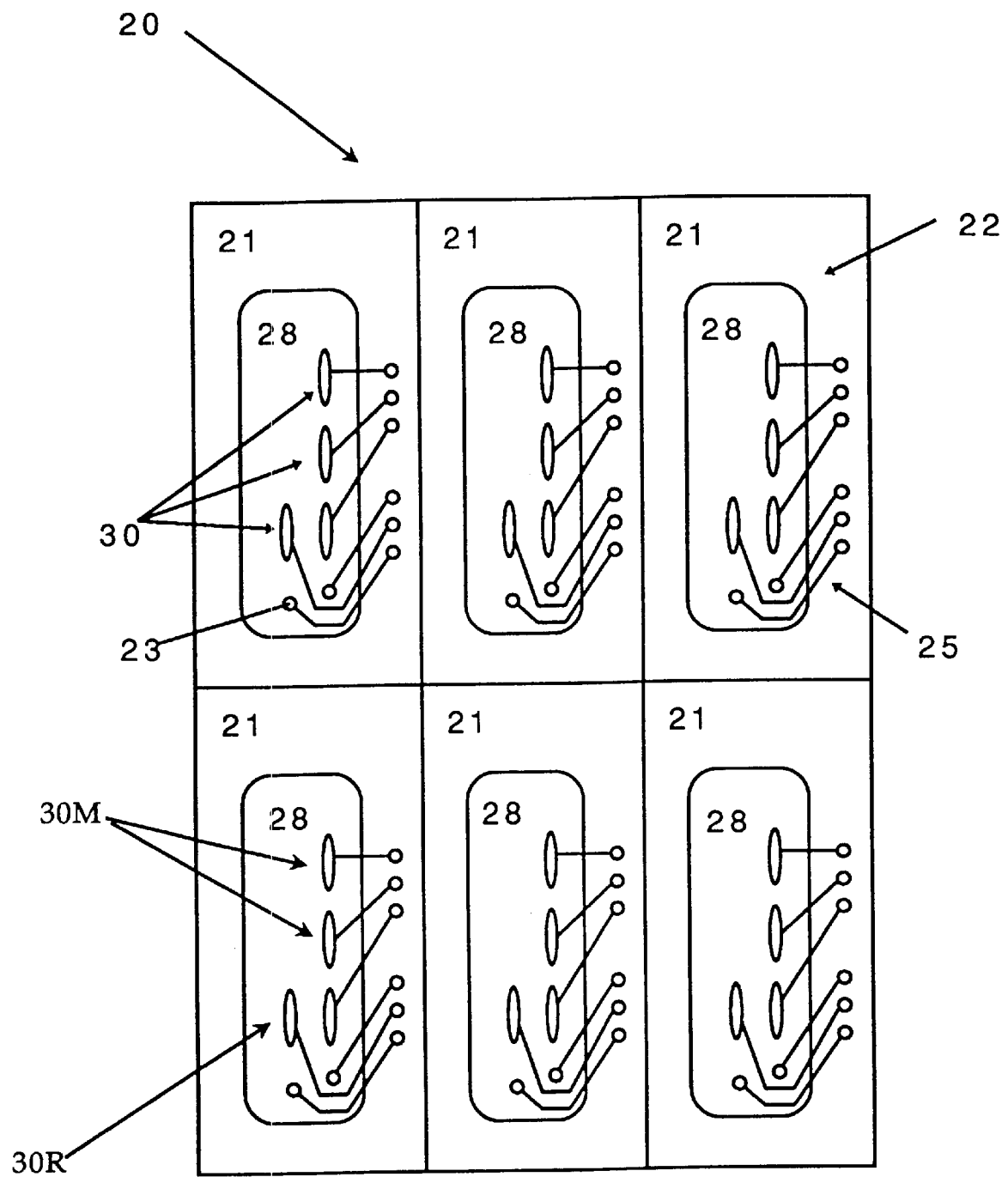
FIG. 1 is a plan view of a plurality of sensor devices embodying the present invention.

FIG. 1 shows a sensor substrate 20 comprising a number of individual sensor bases 21 arrayed in a regular pattern, the bases 21 being defined by scribing the regular pattern onto a contiguously formed single manufacturing piece suitable for handling by automated production equipment. After manufacturing processes are completed, the sensor bases 21 may be separated into a number of individual sensors. Each of the sensor bases 21 has integrated thereon in planar arrangement a single sensor device 22 comprising a plurality of conductive paths 25 deposited in patterns terminating in electrical contacting pads 23, the conductive paths 25 originating in sensor elements 30, sensor elements 30 being comprised of individual layers 24, 26, and 28 (best seen in FIGS. 2a and 2b). The sensor elements 30 are designed to perform either reference or measuring tasks and are preferably disposed in banks or rows of linearly disposed sensor elements with the sensor elements 30 being a reference function sensor element 30R being on one side or row and the sensor elements 30 being a detecting or measuring function sensor element 30M for the analyte on the other side or row.

Figure 1A:
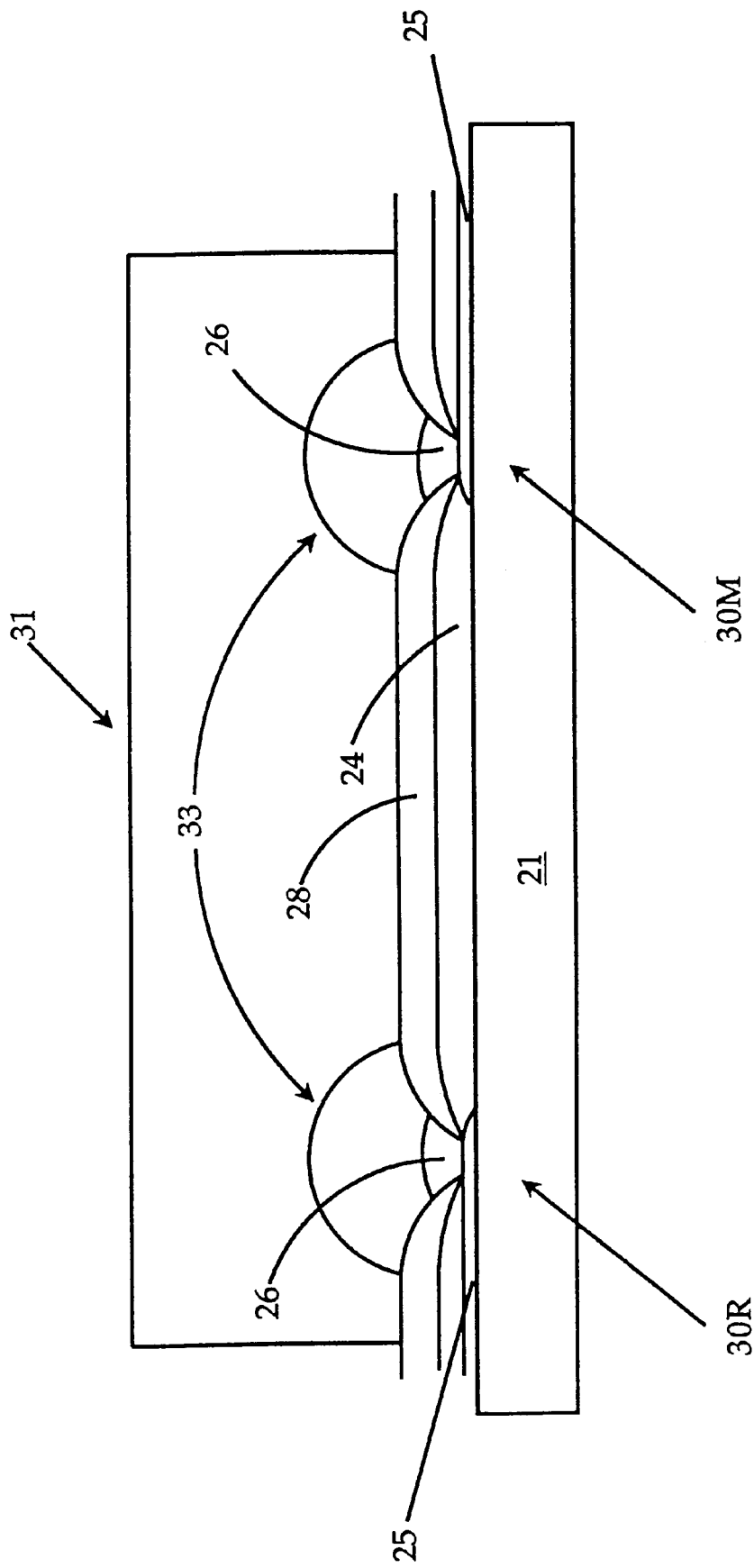
FIG. 1a is a cross-section of sensor device embodying the present invention.

In a commercial application, the sensor elements 30 may be used advantageously within a chemical analyzer, in combination with a flow channel member 31 (see FIG. 1a) having grooves 33 positioned over the reference function sensor elements 30R and measuring function sensor elements 30M and joined together at one end of each groove, thereby defining liquid flow channels (not shown). The upper surface of the sensor membrane layer 26 is thusly in fluid and electrolytic contact with biological sample liquids supplied through the grooves 33. The amount of analyte in a sample fluid may be determined by using the sensor devices in pairs, with one sensor device being exposed to a reference solution containing a known amount of analyte, and the other being exposed to a sample solution containing an unknown amount of analyte. U.S. Pat. No. 5,284,568, assigned to the assignee of the present invention, is illustrative of such a device. Using well known calibration techniques, an assay may be performed in a comparative or differential method of measurement to determine the levels of an analyte in sample fluids.

Figure 2A:
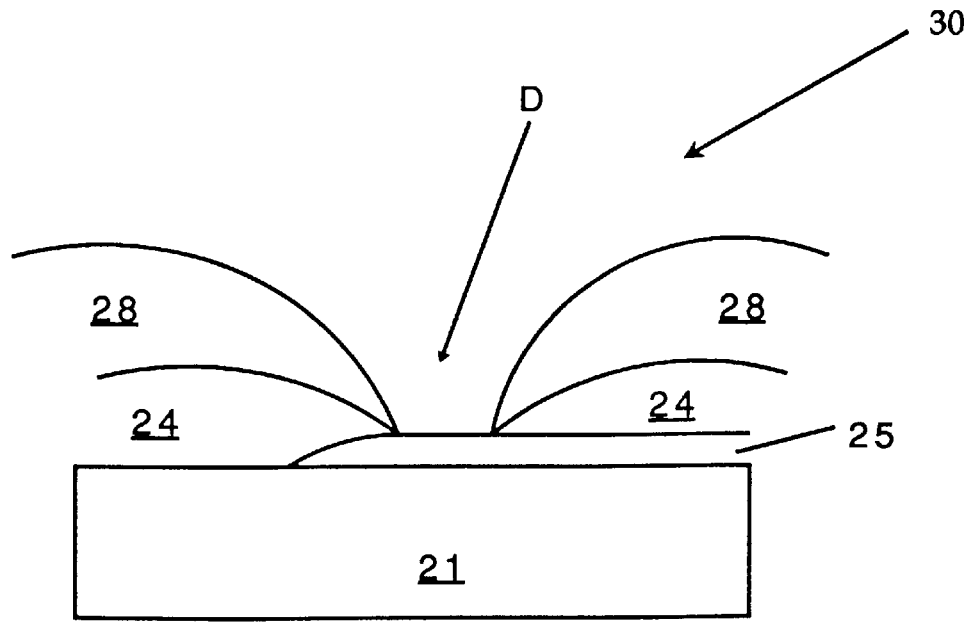
FIGS. 2a and 2b are cross-sectional views of a single sensing element of the sensor devices of FIG. 1.
Figure 2B:
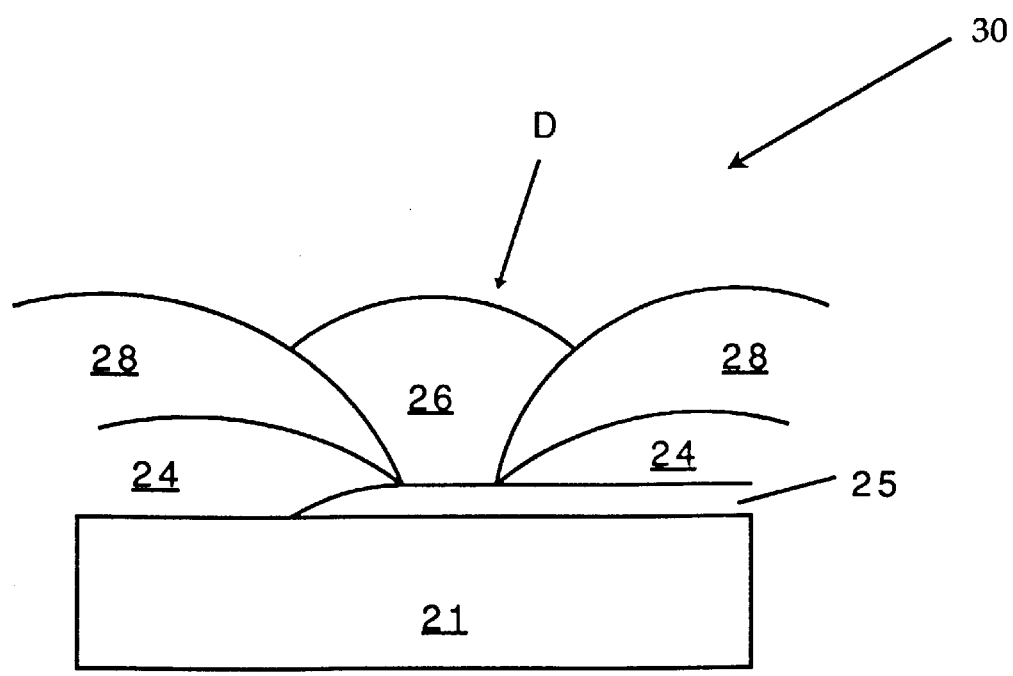

As best seen in FIG. 2a, each sensor element 30 comprises a first dielectric layer 24 and a second dielectric layer 28 formed thereon in contact with a conductive electrode path 25, the layers 24 and 28 having patterns of openings therein, the openings in the patterns aligned to form a "well-like" cavity, generally indicated by the letter "D". As seen in FIG. 2b, a sensor membrane 26 may then be applied within the cavity D formed by openings in the layers 24 and 28 and is positioned in contact with the electrode path 25. The process for making such a device, preferably using conventional thick film screen printing techniques and suitable drying means, is well known in the art, for example, as described in U.S. Pat No. 4,454,007, assigned to the assignee of the present invention. By way of example, one first deposits the conductor layer 25, typically using a conventional silver conductor paste, for instance series QS175, available from E. I. du Pont de Nemours & Co., Wilmington, Del., then the first dielectric layer 24, typically a conventional ceramic dielectric paste, for instance series QS482, the second dielectric layer 28 also for instance series QS482, and finally the sensor membrane layer 26. The purpose of the dielectric layers 24 and 28 is to establish a cavity D of sufficient depth, generally between 20 and 40 microns, to accommodate the minimum required thickness of sensor membrane layer 26 (See FIGS. 2a and 2b). Optionally, an interfacial layer generally composed of a conductive metal and conductive metal-salt compounds may be disposed between the conductor layer 25 and the sensor membrane layer 26 to stabilize the conductor/membrane interface.

A variety of ion selective membrane compositions may be used for the membrane layer 26, generally comprising an ionophore for an ion of interest, a compound capable of dissolving the ionophore and a supporting matrix comprised of one or more binder materials. The matrix can be any material which is capable of forming a film of sufficient permeability to produce, in combination with the ionophore and solvent, analyte ion mobility across the film. U.S. Pat. No. 5,401,377 contains information about the various chemical constituents and applicable production processes useful in production of ISE sensors having an ion-sensitive member in direct contact with an electrical conductor and is generally indicative of the state-of-the art.

Useful ionophores include ion carriers such as hemispherands, crown ethers, monensin and esters thereof (e.g. methyl-monensin), and others known in the art. Ionophores also include ion-exchangers, such as polymeric ion-exchange materials, and water insoluble salts. The choice of ionophore will depend on the nature of the ions to be determined, e.g. valinomycin for potassium, methyl-monensin for sodium, tri-n-dodectyl-methylammonium for chloride, etc. The ionophore is dissolved by one or more organic solvents thereby providing sodium ion mobility. If a hydrophobic binder is used as the supporting matrix, the solvent must be compatible with the binder. The solvent is sometimes identified in the art as a carrier solvent. Useful solvents include phthalates, sebacates, aromatic and aliphatic ethers, phosphates, mixed aromatic aliphatic phosphonates, adipates, nitrated ethers or esters or mixtures thereof, and others known in the art. The polymeric matrix materials were chosen from a variety of substances selected from the group consisting of polyvinylchloride, copolymers of polyvinylchloride, polyurethanes, methacrylate polymers, acrylic polymers, and polymers compatible with polyvinylchloride, and mixtures thereof, with polyvinylchloride being generally preferred.

Useful membranes including hydrophobic binder materials, an ionophore, and solvating solvents are prepared using known film-coating or casting or screen printing techniques. Materials including synthetic and natural polymeric materials, such as poly(vinyl chloride), carboxylated poly(vinyl chloride), poly(styrene-co-styrene sulfonic acid), poly(vinyl chloride-co-styrene sulfonic acid), poly(vinyl chloride-co-styrene carboxylic acid) and the like may be used to advantage. High molecular weight poly(vinyl chloride) has been successfully used in the practice of this invention. Useful plasticizers include 2-ethyl hexyl adipate and/or dioctyl sebacate. One problem encountered with the use of such polymeric materials occurs as a consequence of their optical characteristics. In particular, the optical transmissivity of such polymeric materials generally falls within a range of values that are essentially transparent to the illuminating systems used in commercial optical inspection systems. A related problem occurs whenever the optical reflectivity of the membrane falls within a range of values that are essentially equivalent to that of the underlying dielectric layers and/or of the substrate material thereby causing a vision system to be unable to reliably differentiate between the membrane and dielectric layers. The problem of inadequate contrast between layers can be addressed through the use of optical inspection systems designed to detect fluorescence in combination with membranes modified to fluoresce differentially from the underlying layers.

The preferred class of fluorophores for this application is the class of coumarins. These appear not to interfere with the accuracy of the sensors, compared to fluorophores from the rhodamine or fluorescein classes. Within the coumarin class, certain members have been discovered to have superior fluorescent efficiency that would not be anticipated from their structural similarities or from the spectral or fluorescence data provided by the vendor's specifications for these products. The preferred fluorophores of the present invention are selected from the class of 7-amino-coumarin derivatives generally having the structure shown below:

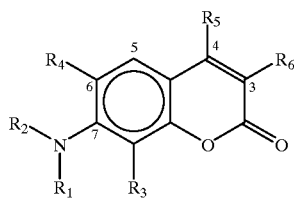

wherein $R_1$, $R_2$, $R_3$, and $R_4$ are hydrogen, alkyl or alkylene groups, and $R_5$, and $R_6$ are a hydrogen, alkyl, alkylene, haloalkyl, aryl or aromatic, halo, carboxyalkyl, oxo-alkyl, or cyano substituent. A preferred fluorophore, coumarin 6 (3-(2'-benzothiazolyl)-7-N,N-diethylaminocoumarin), has been discovered to have superior fluorescence in the membranes without degrading the utility of ISE sensors produced therewith. The structure of coumarin 6 is shown below:

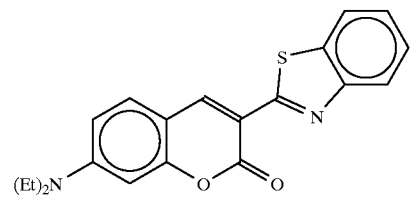

Another preferred coumarin is coumarin 314 (1,2,4,5,3H, 6H,10H-Tetrahydro-9-carbethoxy(1)benzopyrano(9,9a,1)-gh)quinolizin-10-one) having structure shown below:

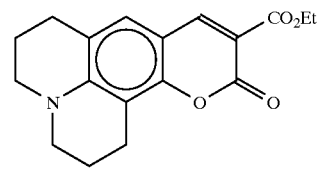

Fluorescent Sensor Membranes

Materials

The sensor design, the substrate and the polymeric paste used to prepare the undried membranes were prepared according to the process described in U.S. Pat. No. 5,522, 978 assigned to the assignee of the present invention and hereby incorporated by reference. Rhodamine 6G, fluorescein, methylene chloride, isophorone, carboxylated polyvinyl chloride, silica, trdodecylmethylammonium chloride, and glycidoxypropyltrimethoxysilane can be obtained commercially from the Aldrich Chemical Co. (Milwaukee, Wis.).

The coumarins were obtained commercially from Acros Organics (New Jersey). The sodium ionophore (Fluka III), valinomycin, dioctyl adipate, and potassium tetra (chlorophenyl)borate, can be obtained from Fluka Chemika-BioChemika (Ronkonkoma, N.Y.).

The performance of the completed sensor assemblies was tested using standard operating protocols on a Dimension® AR clinical chemical system obtained from Dade Chemistry Systems (Newark, Del.). Ultraviolet spectra were obtained using an HP model 8452A diode array spectrophotometer, available from Hewlett Packard Co, (Palo Alto, Calif.).

Analytical Performance of ISE Sensors:

Electrolyte testing was done by installing the integrated sensor arrays on a Dimension® system that was equipped with pumps, calibrants, sensor cartridges and appropriate software obtained from Dade Chemistry Systems Inc., Newark, Del. The testing was done by first calibrating the cartridges with two levels of each electrolyte, and then running a panel of test samples consisting of two levels of aqueous buffered electrolytes, and three samples of serum based control products. The calibrators and verifiers were obtained from Dade Chemistry Systems, Inc., and the control products are Ciba-Corning Co.'s commercial Multi-qual® reagents. Medfield, Me. The aqueous buffered samples are Dade's commercially available "verifier 1" (V1) and "verifier 2 (V2). The control products had multilevel concentrations of 1, 2, and 3, respectively (MQ1, MQ2, and MQ3). The verifier concentrations were determined by comparison to standards based upon gravimetrically determined quantities of pure sodium and potassium salts. The control product concentration assignments were determined by comparison to multiple lots of sensors made without fluorophores.

EXAMPLE 1
Membrane Paste Preparation
1A: Non-fluorescent Paste Compositions:

The pastes used to prepare the ion selective membranes before incorporation of an ionophore were made by mixing the ingredients listed in Table 1 below:

TABLE 1

| Ingredient | Paste Weight Compositions | | |
|---|---|---|---|
|  | Sodium | Potassium | Chloride |
| Fluka Na III | 0.9% | N/A | N/A |
| Valinomycin | N/A | 0.9% | N/A |
| cPVC* | 8.4% | 8.4% | 8.6% |
| Dioctyl adipate | 17.0% | 17.0% | N/A |
| SiO$_2$ | 5.1% | 5.1% | 11.3% |
| Silane** | 3.0% | 3.0% | 2.9% |
| Dichloromethane | 3.9% | 3.9% | N/A |
| Isophorone | 61.6% | 61.6% | 62.1% |
| TDMAC*** | N/A | N/A | 15.0% |
| Borate**** | N/A | 0.005% | N/A |

*caboxylated polyvinyl chloride
**glycidoxypropyltrimethoxysilane
***tridodecylmethylamonium chloride
****Potassium tetra(chlorophenyl)borate 1B: Fluorescent Paste Composition:

Fluorophores were added to the finished paste compositions of example 1A to give a concentration of fluorophore equal to 250 μg/g. After removal of the solvents (isophorone and dichloromethane), the concentration was ≈710 μg/g in the sodium sensor membrane. The fluorophores shown in Table 2 were then evaluated.

TABLE 2

| Example | Fluorophore | Fluorophore Solvent |
|---|---|---|
| 1B.1 | Rhodamine 6G | Methanol |
| 1B.2 | Fluorescein | Methanol |
| 1B.3 | Coumarin 6 | Isophorone |

EXAMPLE 2

2A: Rhodamine Containing Sensors

Sensors were prepared using sodium, potassium and chloride paste that contained 250 μg/mL of rhodamine 6G, according to example 1B, Table 2. The results are shown in Table 3 below:

TABLE 3

| | Performance of Sensors with Rhodamine Fluorophore | | | | | |
|---|---|---|---|---|---|---|
|  | Slope (mv/decade) | V1 (mM/L) | V2 (mM/L) | MQ1 (mM/L) | MQ2 (mM/L) | MQ3 (mM/L) |
| Na (found) | <50 | N/A | N/A | N/A | N/A | N/A |
| K (found) | 57.58 | 2.03 | 6.04 | 2.75 | 4.31 | 6.73 |
| Cl (found) | −48.17 | 94.8 | 129.08 | 81.75 | 104.71 | 126.87 |
| Na (assigned) | N/A | 120.0 | 160.0 | 125.31 | 154.72 | 184.72 |
| K (assigned) | N/A | 2.0 | 6.0 | 2.74 | 4.25 | 6.62 |
| Cl (assigned) | N/A | 95.0 | 128.0 | 82.51 | 105.06 | 126.66 |

The performance of the sodium sensor was unsatisfactory for the rhodamine containing composition, in spite of the low concentration of the fluorophore compared to the ionophore. Because of the sensitivity of the sensor membrane to its constituents, it was expected that some level of rhodamine would interfere with the performance of the sodium sensor, it is surprising that the low level tested in this example would interfere as demonstrated. The calibration slope was less than 50 mV/decade, compared to a typical response of 57–60 mV/decade when no fluorophore is added. Also, the potassium response was slightly elevated by at least one standard deviation for the MQ2 and MQ3 results compared to the values assigned with fluorophore free sensors.

2B: Fluorescein Containing Sensors

Sensors were prepared using sodium, potassium and chloride paste that contained 250 μg/mL of fluorescein added as a fluorophore, in a similar manner as in Example 1B. These sensors were subjected to the same test panel as in Example 2A using the same verifiers and control products. The results are shown in Table 4 below:

TABLE 4

Performance of Sensors with Added Fluorescein Fluorophore

|  | Slope (mv/decade) | V1 (mM/L) | V2 (mM/L) | MQ1 (mM/L) | MQ2 (mM/L) | MQ3 (mM/L) |
| --- | --- | --- | --- | --- | --- | --- |
| Na (found) | 57.79 | 120.92 | 161.12 | 130.16 | 160.70 | 191.41 |
| K (found) | 58.88 | 2.07 | 6.02 | 2.75 | 4.27 | 6.65 |
| Cl (found) | −48.61 | 95.92 | 129.62 | 82.07 | 104.57 | 126.39 |
| Na (assigned) | N/A | 120.0 | 160.0 | 125.31 | 154.72 | 184.72 |
| K (assigned) | N/A | 2.0 | 6.0 | 2.74 | 4.25 | 6.62 |
| Cl (assigned) | N/A | 95.0 | 128.0 | 82.51 | 105.06 | 126.66 |

In all cases, the sensors with added fluorescein gave calibration slopes that were comparable to what is obtained with sensors having no fluorophore. The sodium sensor gave inaccurate results with the control products MQ1, MQ2, and MQ3. The results were elevated by 5–7 mv/L compared to the values assigned with sensors having no fluorophore.

2C: Coumarin 6 Containing Sensors

Sensors were prepared using chloride, potassium, and sodium pastes that contained 250 μg/mL of coumarin 6, in the same manner as in example 1B.3. These were subjected to a test panel of the same verifiers and control products previously employed. The results are shown in Table 5 below:

TABLE 5

Performance of Sensors with Added Coumarin 6 Fluorophore

|  | Slope (mv/decade) | V1 (mM/L) | V2 (mM/L) | MQ1 (mM/L) | MQ2 (mM/L) | MQ3 (mM/L) |
| --- | --- | --- | --- | --- | --- | --- |
| Na (found) | 59.7 | 120.4 | 158.8 | 123.8 | 147.3 | 172.4 |
| K (found) | 59.4 | 2.04 | 5.94 | 2.36 | 4.12 | 6.31 |
| Cl (found) | −48.7 | 94.6 | 128.7 | 80.8 | 102.0 | 126.5 |
| Na (assigned) | N/A | 120.0 | 160.0 | 123 | 147 | 172.5 |
| K (assigned) | N/A | 2.0 | 6.0 | 2.35 | 4.1 | 6.28 |
| Cl (assigned) | N/A | 95.0 | 128.0 | 80.1 | 102 | 126.8 |

All of the sensors gave accurate results with both the verifiers and control products. The calibration slopes were also satisfactory.

EXAMPLE 3

3A: Coumarin Fluorescence:

Samples of fluorophore containing membranes were prepared for spectral studies. These were made using the formulation for sodium paste described in example 1B, with two changes; the silane coupling agent and the Fluka III ionophore were omitted. The concentration of fluorophore in the paste was 250 μg/mL.

TABLE 6

| Example | Fluorophore | Fluorophore Solvent |
| --- | --- | --- |
| 3A.1 | Coumarin 6 | Isophorone |
| 3A.2 | Coumarin 314 | Isophorone |

Figure 3:
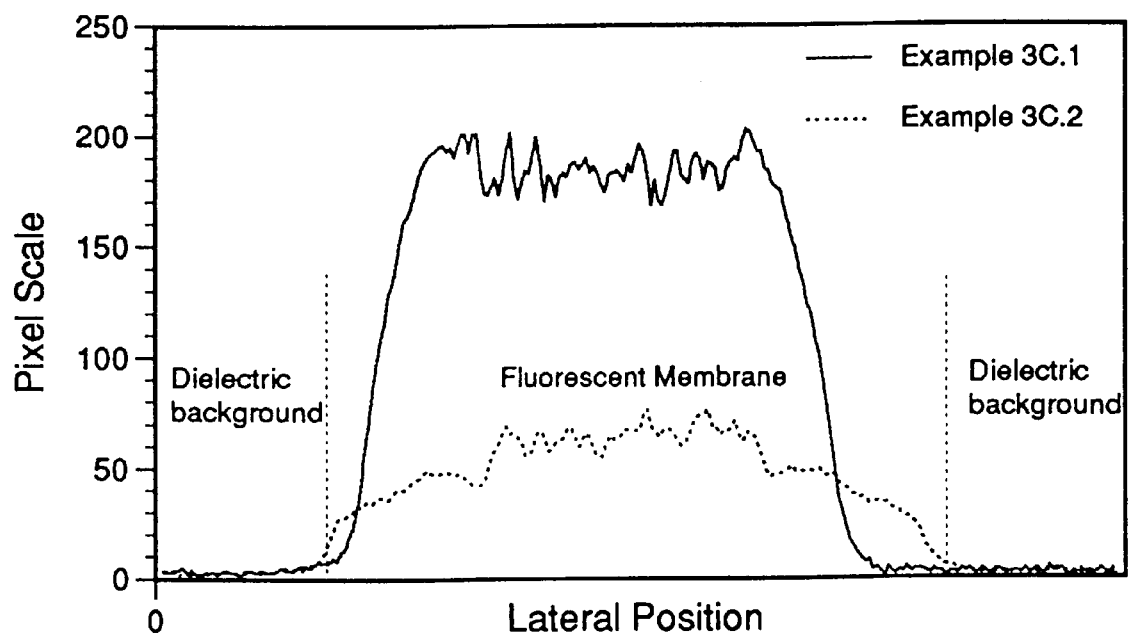
FIG. 3 is a chart representing the results of machine vision inspections from practicing the present invention.

3B: Membrane Fluorescence Response:

The paste samples 3A.1 and 3A.2 were dispensed into the preformed wells of ceramic substrates. Using the apparatus described hereinafter, the undried membranes were illuminated and viewed with a video imaging device attached to optical elements. The images were digitized to give pixel responses having 256 gray scale levels. The digitized pixel values, indicative of the amount of fluorescence response from the selected fluorophores, are shown as a function of lateral position across the membrane in FIG. 3. Starting from the left edge of the graph, the first section of the curves show a low background pixel response of the ceramic dielectric where no fluorescent membrane paste was applied. The left hand vertical dotted line indicates the boundary edge of the area covered with paste. Continuing across the graph, representing the sensor, the pixel scale response rises steeply to a maximum level, reaches a plateau in the area of the maximum membrane thickness, and then drops to the background response level, at the right side of the membrane.

The response from background lighting in areas not covered with paste gave pixel response values of about 45 units. This was subtracted from the values seen in the wet membrane, to give the results shown in FIG. 3. The response with example 3A.1, using the preferred coumarin 6 surprisingly was about 4× stronger than with the other example, 3A.2.

Sensor Assembly

Figure 4:
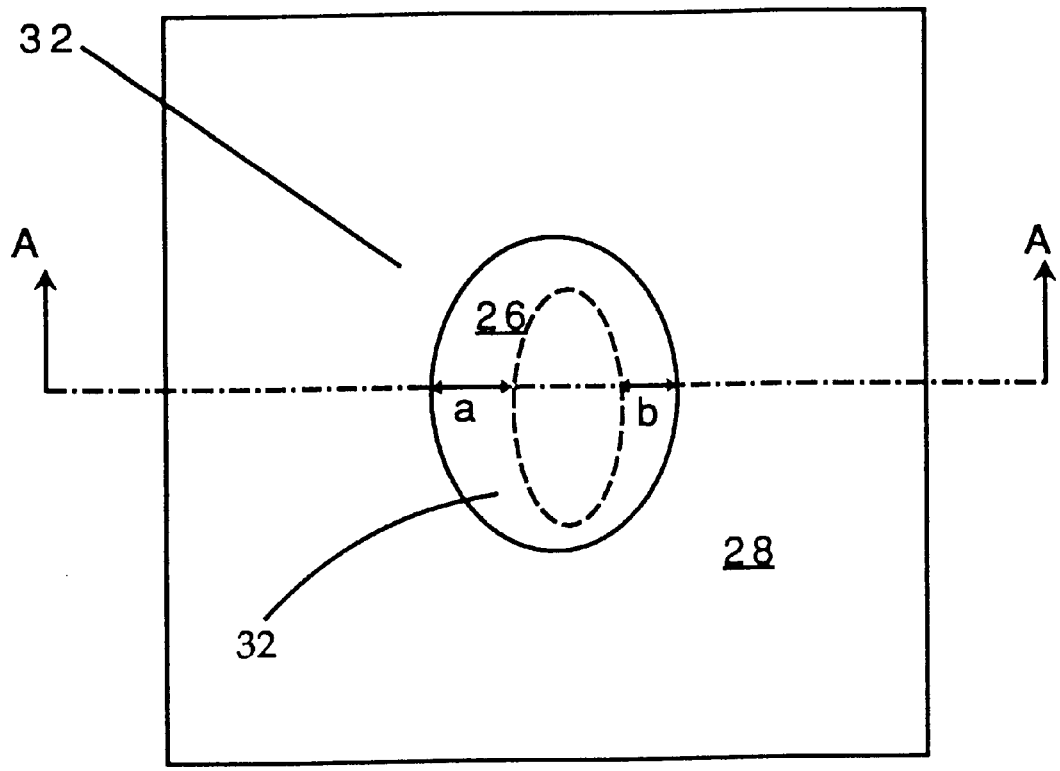
FIG. 4 is a plan view of a single sensing element of the sensor devices of FIG. 2b illustrating different registration situations.
Figure 5:
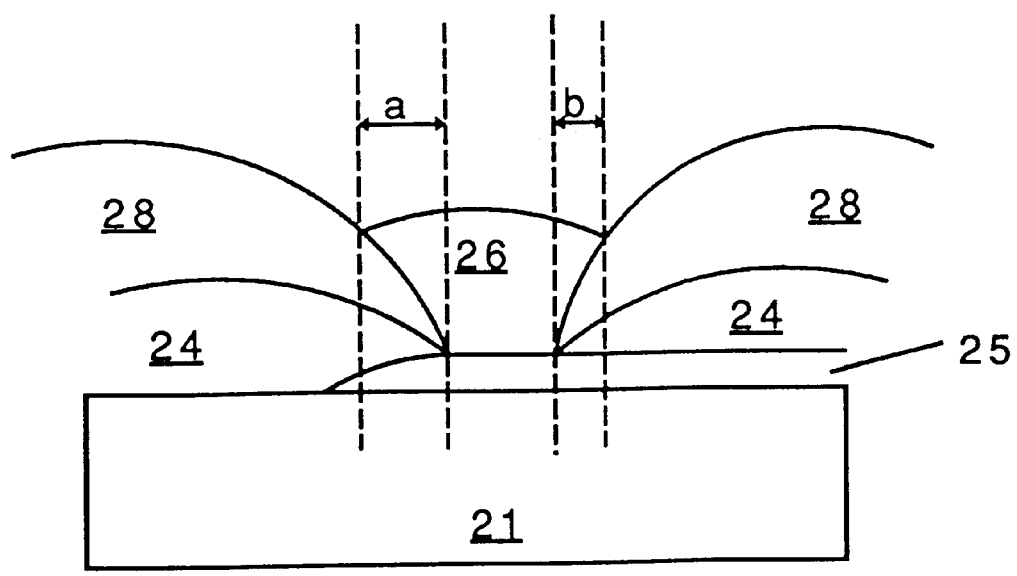
FIG. 5 is a cross-sectional view showing alignment dimensions of a single sensing element of the sensor devices of FIG. 1.

FIG. 4 is an enlarged and somewhat simplified view of a single sensor element 30 and, taken with the cross-section shown in FIG. 5, illustrate a typical pattern alignment obtained for a single sensor element made using the polymeric matrix composition of Table 1 having dispersed therein an ion exchange ionophore of at least 0.001% and less than about 2% by weight of at least one of the preferred coumarin fluorophores selected from the group of 7-aminocoumarin derivatives as more fully described herein. It is important for proper functioning of the sensor element 30 that the sensor membrane layer 26 be aligned with and overlap the dielectric layers 24 and 28 to form an annular ring 32 region of overlap that exceeds predetermined minimum dimensions. At the same time, the sensor membrane 26 must be in electrical contact with the underlying conductive path layer 25. In the instance that the device 21 is sized approximately 1 inch by 2 inch, the annular ring 32 region is approximately an oval having dimensions 0.050 by 0.200 inches, while overlap dimensions indicated as "a" and "b" ideally fall into a range, for example from 0.001 to 0.020 inches. The minimum dimensions of overlap that are formed by annular ring 32 region are determined as those overlap dimensions required to provide adequate operating stability. Inadequate overlap increases the possibility for test fluids contained in the fluid channel 34 to diffuse underneath sensor membrane layer 26 and to establish erroneous electrical connections directly with the conductor layer 22.

Figure 6:
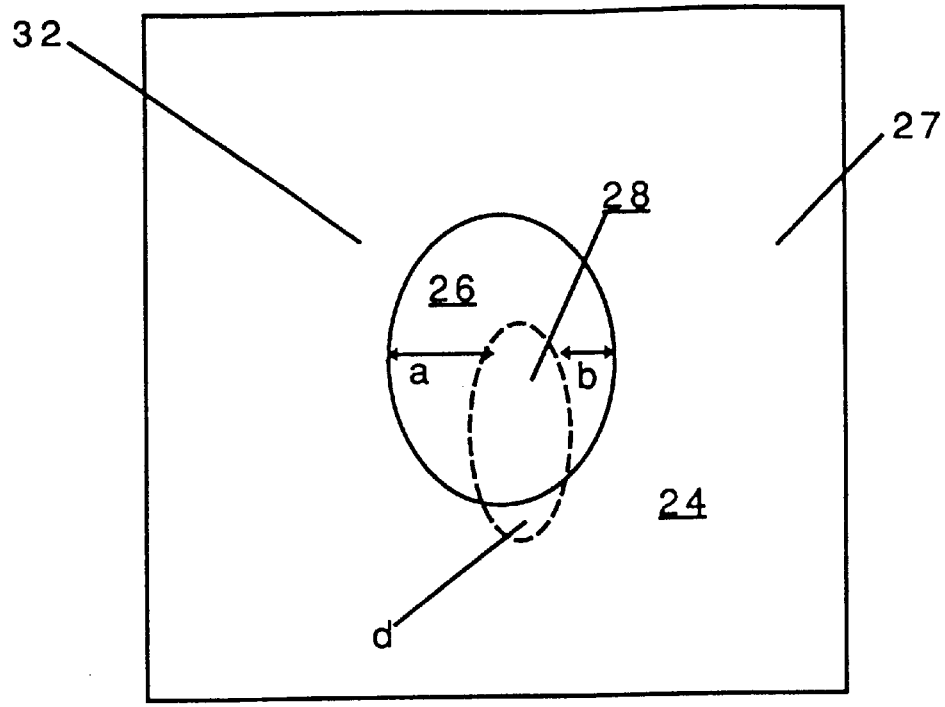
FIGS. 6, 7 and 8 are plan views of a single sensing element of the sensor devices of FIG. 4 illustrating different registration situations.
Figure 7:
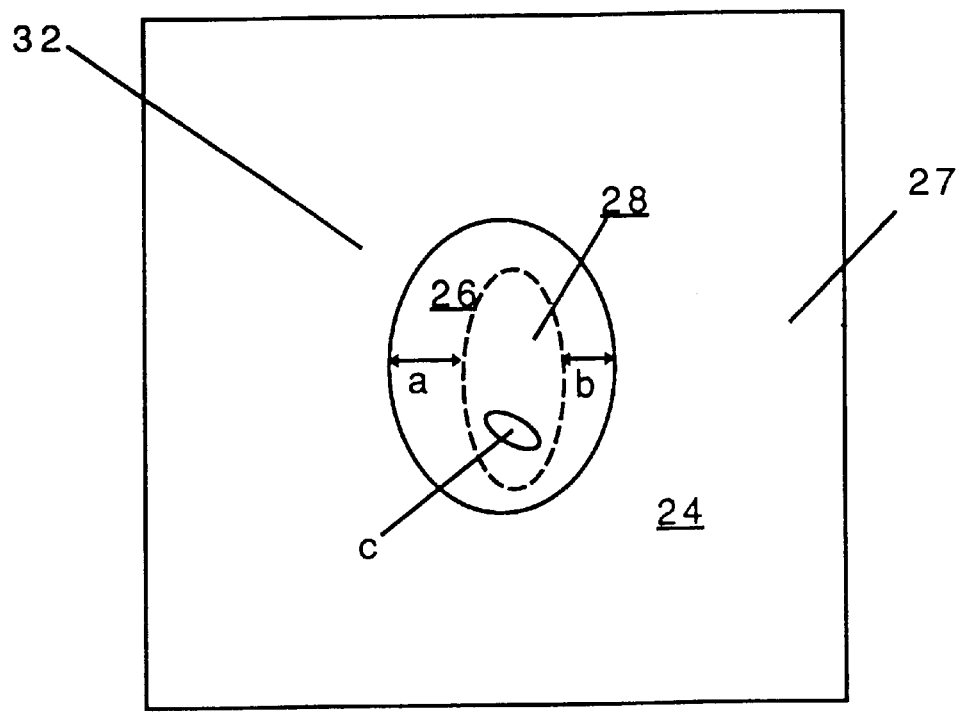
Figure 8:
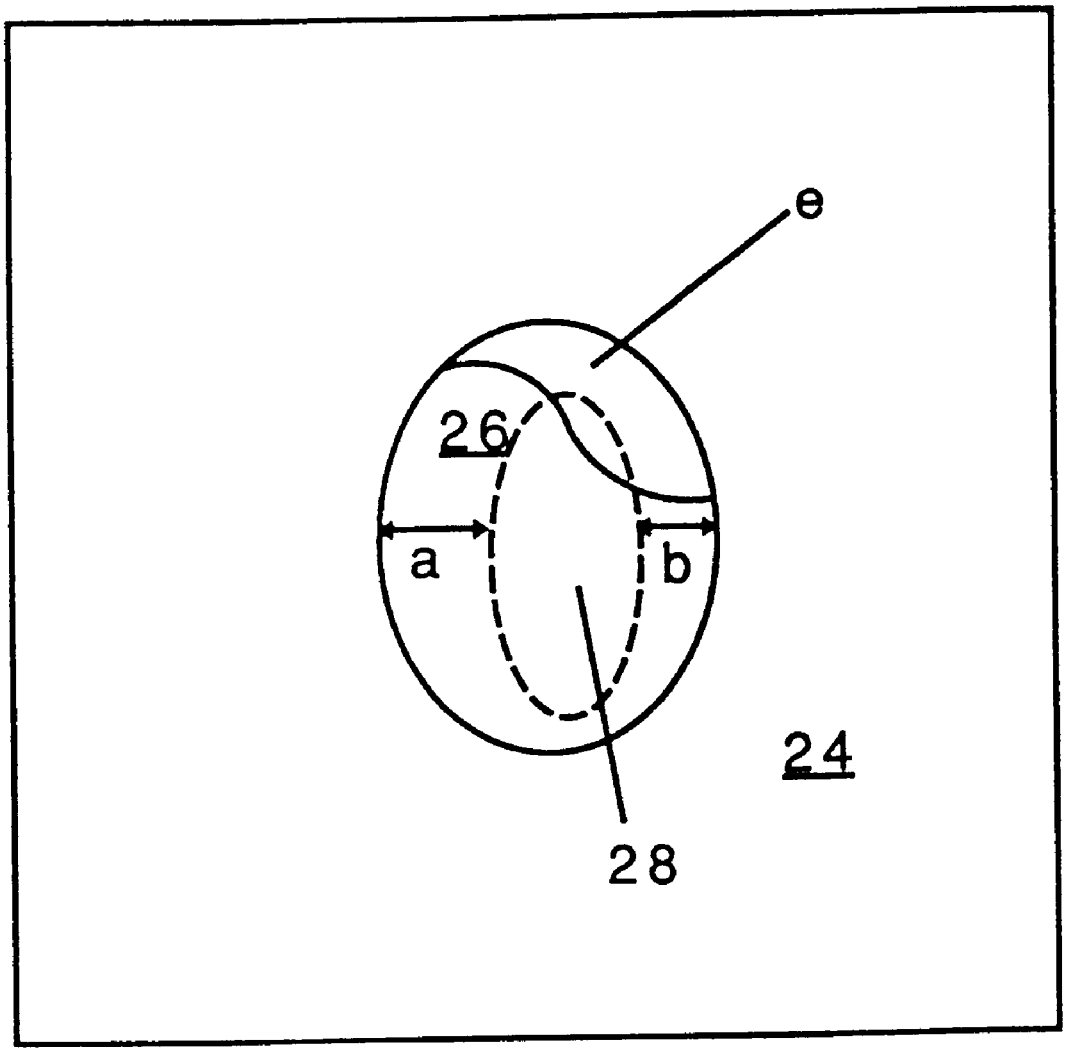

FIGS. 6, 7 and 8 illustrate several of the various defects that may occur from positional inaccuracy of imprinted features. Misregistration of pattern features that may occur from misalignment of the sensor paste layers include a pinhole formed in the sensor membrane layer 26 indicated by the letter "c" in FIG. 7, incomplete coverage of the sensor membrane layer 26, indicated by the letter "d" in FIG. 6 due to misregistration and incomplete coverage of the sensor membrane layer 26, indicated by the letter "e" due to incomplete application of the sensor membrane in FIG. 8.

Preferred machine vision systems used in practicing this invention are generally comprised of a host computer and special-purpose processing hardware having software implemented applications to make it perform the required digital image processing operations. Such systems are available from vendors like Omron Electronics (Schaumburg, Ill.), Allen Bradley (Milwaukee, Wis.), and PPT Vision (Minneapolis, Minn.). The principles involved are well known, for example as explained in "Digital Image Processing", Gregory A. Baxes, John Wiley & Sons, Inc., New York. In particular, image differencing techniques are employed to determine small variations between two images that may appear essentially the same by unaided observation. Using this technique, two images may be compared, pixel by pixel, so that the image portions that are identical will subtract to zero (0). Portions of the images that are different, however, will yield a signal other than zero (0). Conventional image enhancement and analysis techniques may then be applied to determine object shape measurements that characterize the appearance of an image according to pixel distance around the circumference of the image, pixel area of the interior of the image, pixel distances of the major and minor axes of image, count of number of holes that exist in the interior of an image, total pixel area of the holes, and the like. A comparison of these pixel values with predefined maximum and minimal acceptable absolute values is used to judge the quality of the membrane sensor layers. These techniques are well known in the art.

A feature of the present invention is use of dual radiation means to illuminate the sensor to: (1) determine the locations of semi-finished sensor elements using radiation energy outside the fluorophore excitation band; and (2) determine the locations of the corresponding as-deposited sensor membrane paste using radiation energy capable of exciting the fluorophores included in the sensor membrane 26. This allows a comparison between a semi-finished sensor element 30 (like that shown in FIG. 2a) before the uppermost sensor membrane 26 is applied and a finished sensor element 30 (like that shown in FIG. 2b) after the uppermost sensor membrane 26 is applied. This comparison is accomplished by utilizing a first illumination means having radiation selected so that the sensor membrane 30 remains essentially transparent to the image acquiring means in combination with a second illumination means having radiation selected so that the sensor membrane 30 becomes essentially visible to the image acquiring means. Appropriate filters to select the radiation without detracting from the images of the sensor membrane 30 are included. Means for acquisition, enhancement and analysis of the images of the sensor element 30 surface image (not shown) comprise a frame-grabber and a microprocessor, and interface means to permit variable programming of the system's microprocessor-based computer for desired membrane application and inspection tasks through a user-interactive or computer-controlled system of menus. The system is preferably combined with a conventional material handling system typical of piece-parts manufacturing which transports and presents the sensor elements 30 to the machine vision system. These mechanisms, their installation and use are known to those skilled in the art.

Figure 9A:
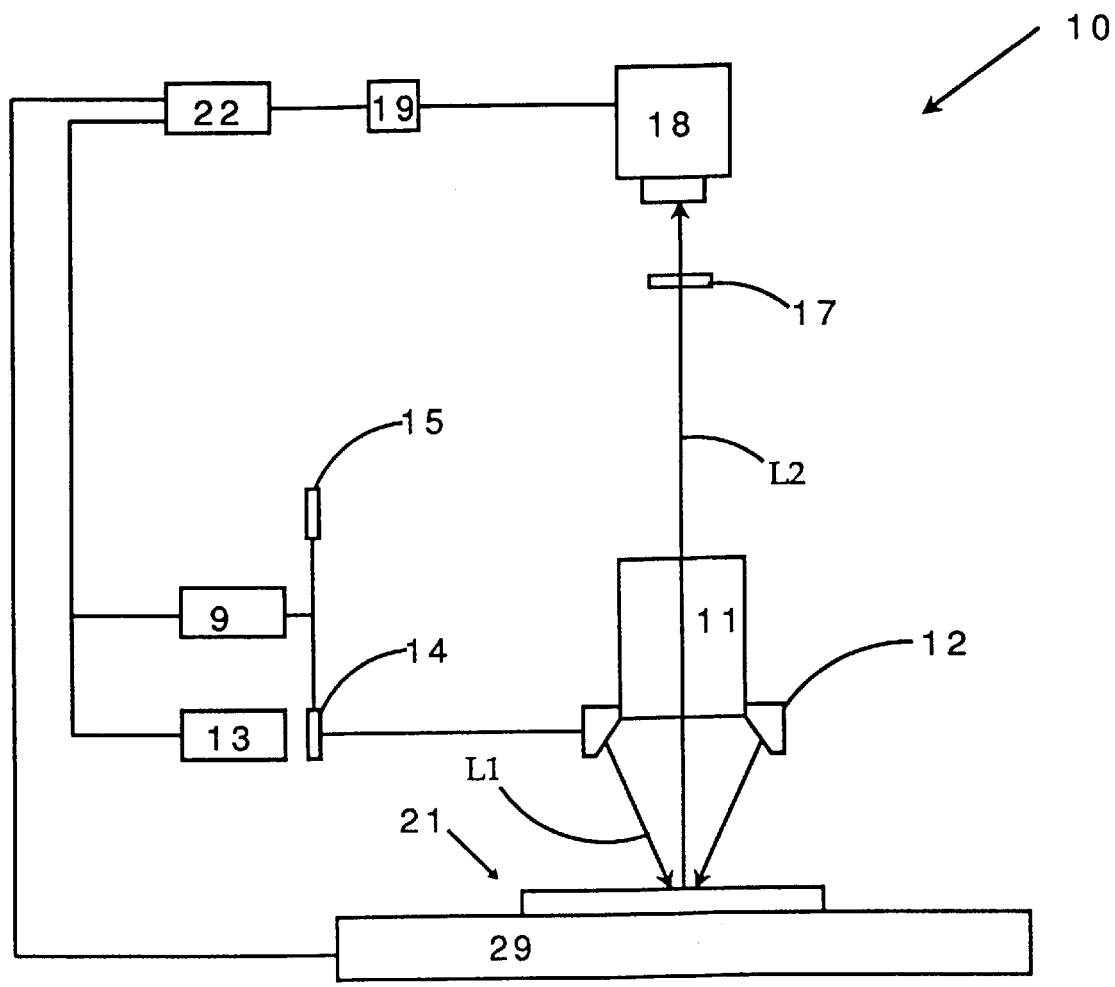
FIGS. 9a and 9b are schematic views of a machine vision system useful in practicing this invention; and, FIG. 10 is a flow chart depicting a method of practicing the present invention.

FIG. 9a shows such an exemplary sensor production system employing machine vision for performing the inspection of sensor substrates 21 enabled by the sensor membrane compositions of the present invention, the substrates 21 being mounted on a conventional, computer controlled "x-y-z" positioning table 29. A radiation source 13, preferably model D-7918 obtained from Scholly Fiberoptik GmBH (West Germany), is adapted to provide a radiation pattern L1 having wavelengths generally in a range from 300 to 700 nm. A first filter 14, for example model 51302 produced by Oriel Instruments (Stratford, Conn.) having bandpass characteristics such that only radiation having wavelengths greater than about 500 nm is passed is positioned proximate to the radiation source 13 to intercept and filter radiation pattern L1 so as to illuminate the semi-finished substrate 21, in particular, the conductor layer 25, and the two dielectric layers 24 and 28. This filtered radiation pattern L1 is distributed from ringlight 12, for instance model 10-1602-03 produced by Ram Optical Inspection (Huntington Beach, Calif.) to illuminate the sensor substrate 21 at an angle from about 20 to 40 degrees relative to the optical axis defined by a direction perpendicular to the surface of the substrate 21.

A shuttle device 9 is adapted to replace the first filter 14 with a second filter 15, for example model 57530 produced by Oriel, the second filter 15 having narrow bandpass filter characteristics such that only radiation having wavelengths preferably centered between about 400 and 500 nm to provide illumination selected to excite the coumarin fluorophores contained in the sensor membrane 26. The filtered radiation L1 is emitted from ringlight 12 to illuminate the sensor substrate 21 at an angle from about 20 to 40 degrees relative to the optical axis.

A radiation emission filter 17, for example model 51302 produced by Oriel having bandpass filter characteristics selected such that only radiation having those wavelengths greater than the representative excitation wavelengths of coumarin fluorophores, preferably between about 400 and 800 nm, is positioned before the image acquiring means 18 to intercept the radiation emitted by an excited fluorophore. Thus, only that radiation having wavelengths emitted by the tagging fluorophore within the sensor membrane 26 are incident upon image acquiring means 18 when the second filter 15 is in use. Image acquiring means 18 preferably comprises a high resolution, solid state, MOS (metal oxide semiconductor) type with asynchronous frame reset capability, for instance model XC77 produced by Sony Corporation (Toko, Japan) equipped with appropriate optical elements. This capability allows the image acquiring means 18 to capture the image of a sensor element 30 with spatial resolution of approximately 0.0003 inches per pixel. A changeover for other sizes/shapes of sensor elements 30 may be accommodated by simply adjusting the vertical positions of the image acquiring means 18 and different optical element 11.

Figure 9B:
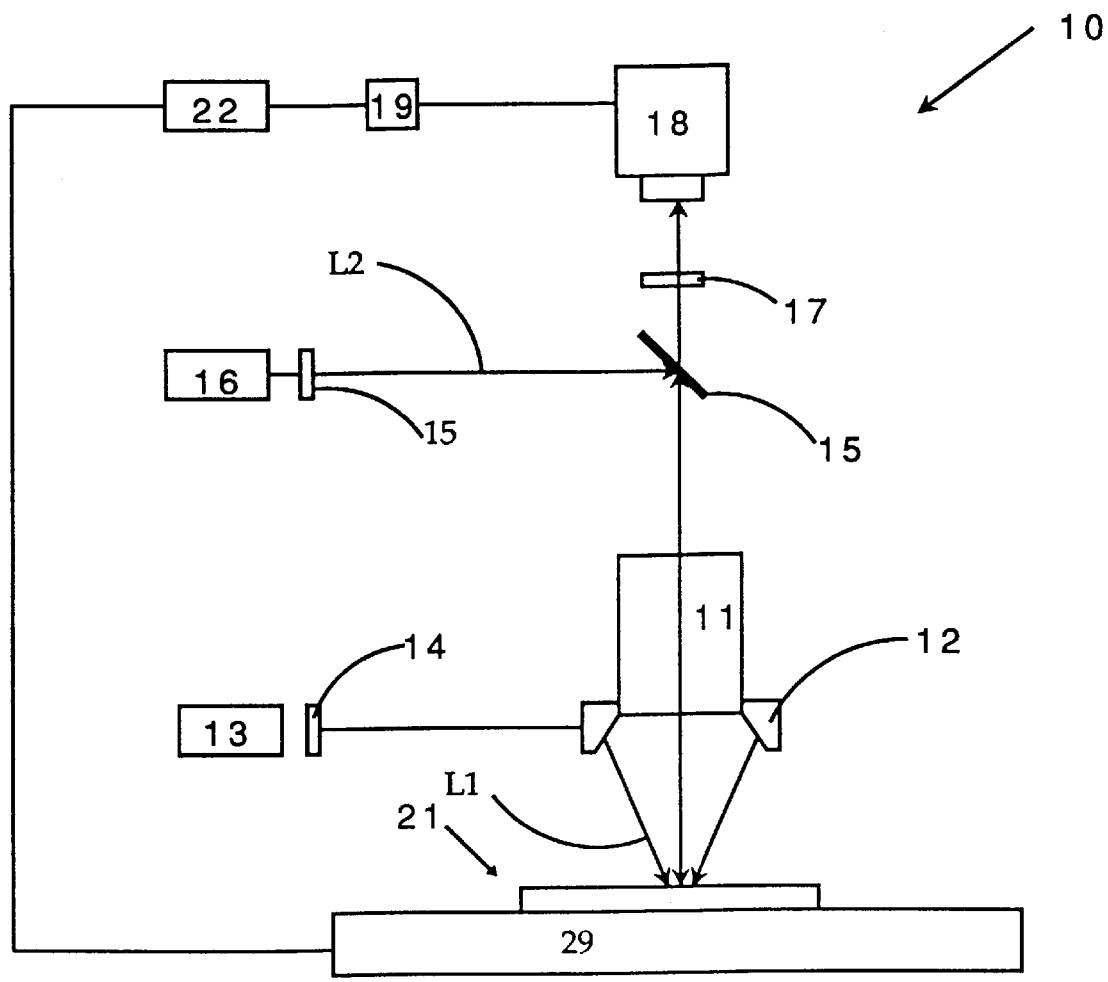

In an alternate embodiment, shown in FIG. 9b, a second illuminating source 16, for example model 50-3500-00 produced by Ram Optical Inspection is employed to provide a beam of radiation generally in a wavelength range from 550 to 650 nm through a beamsplitter 15, for instance model 0102020 produced by Esco Products (Oak Ridge, N.J.) positioned in the optical axis with the split portion of the beam captured by image acquiring means 18 and the reflected portion being normally incident upon the substrate. If used in combination with the preferred arrangement shown in FIG. 9a, this alternate arrangement allows the optimum combination of angularly incident and normally incident radiation upon the substrate from either of the two sources 13 and 16 to provide the highest degree of image contrast and capture, depending upon the surface roughness and optical adsorption/reflection characteristics of the sensor substrate 21 and layers 24, 25, 26, and 28. The arrangement and management of the electronic circuitry of the image acquiring means 18 and the frame-grabber 19 are widely known and the routines of comparing the various images are also well-known.

Figure 10:
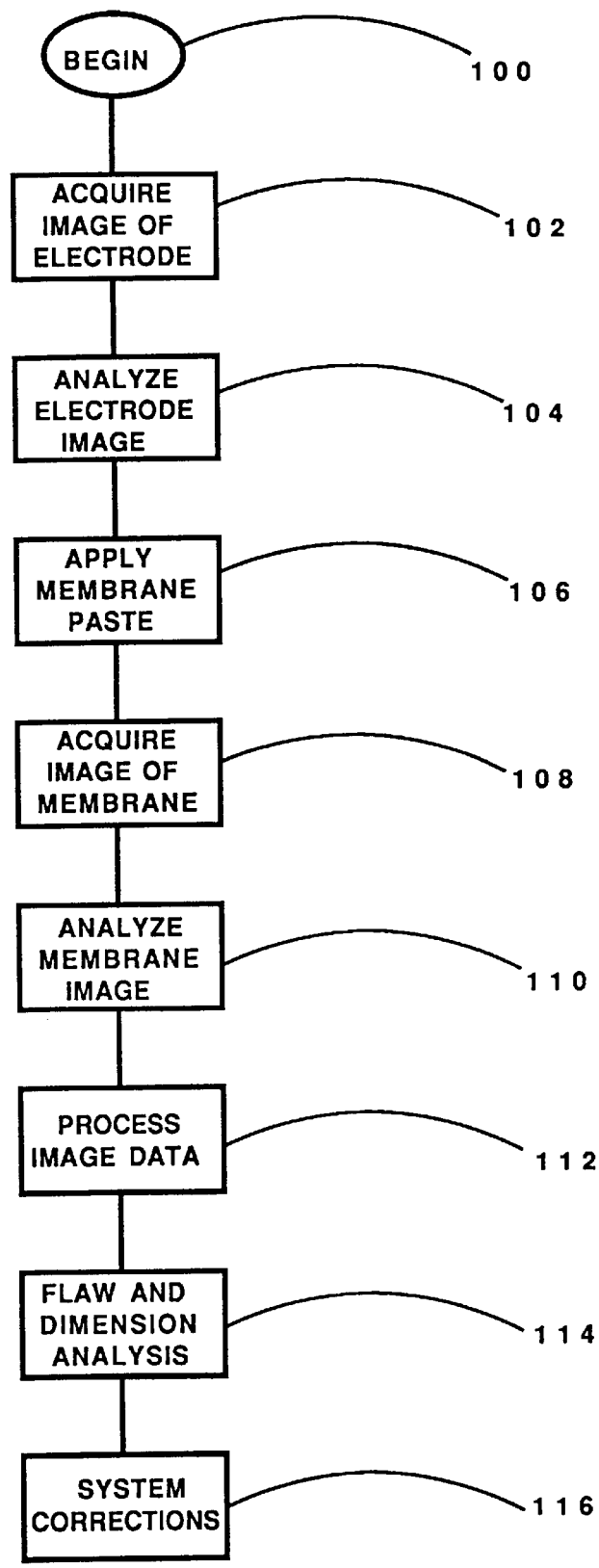

FIG. 10 is a flowchart of a process for determining the target area on semi-finished sensor substrates 21 for sensor membrane layer 26 application, for detecting application flaws within the sensor membrane layer 26 and misregistration of the applied sensor membrane layer 26. The process is further adapted to provide correction information to computer 22. In this process, information regarding the desired positioning of the sensor membrane is determined by illuminating the semi-finished substrate 21 like shown in FIG. 2a in which only the conductor layer 25 and first and second dielectric layers 24 and 28 have been printed onto the sensor substrate 21 with radiation that has been filtered through bandpass filter 14, indicated by step 102. The image acquiring means 18 thus acquires an image of the top surface of the semi-finished sensor element so that the location may be determined of each of the cavities D (FIG. 2a) defined by the dielectric layers 24 and 28 where a sensor membrane 26 is to be applied (FIG. 2b), as shown in boxes 102 and 104.

After the computer 22 determines the precise location of the cavity D, a membrane paste application operation is initiated and the membrane application means (not shown) applies a predetermined amount and pattern of sensor membrane paste within the cavity D as depicted in box 106. Conventional alignment techniques are employed to control the application means to apply the membrane paste in proper alignment on the sensor element 21 so that each cavity D is in communication with no more than one of the conductive elements 25, the membrane 26 being portioned and disposed within said openings so that communication is established between said membrane portion 26 and the conductive elements 25. Application of the membrane composition takes place using dispensing techniques, with equipment available from vendors such as Asymtek (Carlsbad, Calif.), Otto Engineering (Carpentersville, Ill.) and Camalot Systems (Haverhill, Me.).

In the subsequent membrane inspection mode, a sensor element 21 to be inspected is illuminated using radiation in the excitation region of the fluorophore so that the image capture system acquires an image of the sensor membrane 26 as applied to the sensor element 30 and depicted in box 108. The computer 22 and frame-grabber 19 utilized in this invention provides capability for analysis of the digital images in box 110. Consequently, the computer 22 is able to analyze the image of the sensor membrane 26 with respect to the previously generated image in box 102 of the cavity D as depicted in box 112 to determine the degree of coincident alignment by making a conventional flaw and dimension analysis between the two images arising from errors in the application of the sensor membrane 26 as depicted in box 114. Subsequent conventional alignment techniques are employed to control the application of the membrane paste in proper alignment on the sensor element 30 as depicted in box 116.

Applicants have thus discovered that, notwithstanding the performance sensitivity of the ISE sensor membrane to its chemical constituents, certain fluorophores have been found that may be advantageously added to the composition of the sensor membrane 26 without interfering with the performance of chloride, potassium, or sodium sensors. There are two primary requirements for the fluorophore which must be met in such a fluorophore design: first, it must not interfere with the analytical performance of the sensor by causing greater than one percent deviation of the performance of the incorporating membrane; and, second, it must be sufficiently fluorescent within the membrane to provide distinguishable optical contrast relative to the background portion of the sensor under ambient lighting.

The first requirement of the fluorophore is that it cause less than one percent deviation of the amount of measured analyte relative to the analyte concentration determined with compositions having no fluorophore therein. There is general understanding of the compositional requirements of a usable sensor membrane; however, the effects of changes in composition and specific concentrations or chemical structures for the components is not well understood. Since ISE sensors are known to be highly sensitive to the composition of the surface layer of the membrane, it is not obvious or understood why some fluorophores will interfere and others will not, especially at the relatively low concentration of fluorophore used in the Examples herein. The fluorophore is at a concentration of 0.025% in the paste, whereas the specific ionophore for sodium and potassium is ≈1% so that the ionophore is approximately 40× higher in concentration than is the fluorophore. The presence of an ionic species in the membrane of ISE sensors is expected to have an adverse effect on the performance of the sensor. However, it is surprising that at a concentration of less than 2.5% of the active ion-carrier, there is a detectable degradation of performance. Even at this low concentration, the rhodamine and fluorescein examples hereinabove show unexpected, and un-acceptable interference in the sodium sensor. These results are contrary to those expected from the prior art. In the prior art, some ionic species are expected to improve performance. For example, in the case of fluorescein, a lipophilic anion, the expected effect is an improvement in specificity, based upon theory described by Lindner, Erno, et al. in "Response of Site-controlled, Plasticized Membrane Electrodes.", *Analytical Chemistry*, 60 (1988): 295–301. Even at this low concentration, the rhodamine and fluorescein examples hereinbelow show unexpected, and un-acceptable interference in the sodium sensor. While the amino coumarins carry no charge in the native state, side reactions could occur between them and other components of the sensor membrane that would yield ionic products that would interfere with sensor performance. It is not obvious that the amino coumarins are sufficiently chemically inert to be free of such side reactions.

Secondly, a sufficiently high concentration of fluorophore is required within the membrane since the membrane must capture a sufficient amount of the excitation light source to emit an amount of light to permit accurate discrimination between its fluorescence and the background image due to reflected illumination from stray ambient light sources. Unfortunately, the fluorescence of fluorophores is known to be sensitive to self-quenching at the concentration levels required to meet these conditions. Self-quenching is a general term within the art that describes the phenomenon of decreasing fluorescence quantum yield seen as fluorophore concentrations are increased. The processes responsible for this self-quenching are understood in principle, but again, not well enough to accurately anticipate the usefulness of specific compositions.

Another difficulty faced in selection of the fluorophore is that in addition to self-quenching, non-specific chemical processes take place during bonding between the fluorophore and the silane coupling agent used to provide covalent linkage of the membrane to the dielectric of the sensor coupling agent. These non-specific chemical processes generally act to reduce the yield of fluorescence an unpredictable amount.

Surprisingly, certain fluorophores have been successfully incorporated into the sensor membrane 26 as shown in the preceding Examples. Compounds from the coumarin class of fluorophores have proven effective in rendering a detectable fluorescent emission from the normally transparent sensor pastes as described hereinafter without causing greater than one percent interference with the electrochemical response of the membrane. The dyes used in the Examples are all strongly fluorescent when measured at low concentrations in common solvents. For example, the quantum yields for fluorescence for the two coumarins described above are 85% for coumarin 6, and 77% for coumarin 314, (Eastman Laser Products Dataservice Publication JJ-169, 1977, Kodak Optical Products, Eastman Kodak Company, Rochester, N.Y.) Rhodamine and fluorescein compositions were expected to be useful in a ISE sensor, based on the fluorescence obtainable therewith at a low concentration; however, experimental tests described above unexpectedly determined that they caused greater than one percent errors in the analytical performance of the sensors at these low concentrations.

It is within the scope of the present invention to employ other sensor membrane compositions to enhance visualization of various constituents of ion selective electrodes. For instance, by using two different fluorophores in two membrane layers applied successively in a lower and upper relationship, an optical comparison of the relative alignment and integrity of the two layers can be made using essentially the same image acquisition and analysis techniques described herein. Alternatively, by using a fluorophore in the lower layer, and using a light absorbing agent capable of substantially blocking the incident radiation in the upper layer, the relative alignment and integrity of the two layers may be determined using the image acquisition and analysis techniques described herein. The agent, for example an inert phthalocyanine pigment, must also cause less than one percent deviation upon the performance of the membrane layer.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification.

What is claimed is:

1. A method of assembling an ion selective device for sensing the presence of an analyte, the device comprising a planar substrate having in sequence thereon, a plurality of conductive elements, at least one dielectric layer having a plurality of openings forming a cavity therethrough, and a membrane comprising a polymeric matrix, an ion exchange ionophore, and less than 0.001% and 2% by weight of at least one fluorophore, said fluorophore being essentially unaffected by the presence of said analyte, said fluorophore being selected from the class of 7-aminocoumarin derivatives having structure shown below:

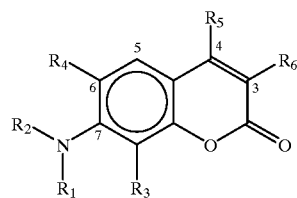

where $R_1$, $R_2$, $R_3$, and $R_4$ are hydrogen, alkyl or alkylene groups, and $R_5$, and $R_6$ are hydrogen, alkyl, alkylene, haloalkyl, aryl, halo, carboxyalkyl, oxo-alkyl, or cyano, the membrane portioned and disposed within said openings, the method comprising:

applying the plurality of conductive elements onto the substrate applying at least one dielectric layer over the conductive elements;

applying the membrane within the openings formed within the dielectric layer so that communication is established between said membrane portions and said conductive elements; and, using a machine vision measurement apparatus adapted for determining the positioning of the openings formed within the dielectric layer and controlling the applying of the membrane within the openings, the machine vision measurement apparatus having illumination means to firstly determine the locations of the openings using radiation having energy outside the excitation band of said fluorophore and to secondly determine the locations of the membrane within the openings using radiation having energy capable of exciting the fluorophore included in the sensor membrane, so that the process for applying of the membrane within the openings may be optimized and controlled.

* * * * *